United States Patent
Lahorkar et al.

(10) Patent No.: US 9,539,189 B2
(45) Date of Patent: Jan. 10, 2017

(54) PHOTOPROTECTIVE PERSONAL CARE COMPOSITION

(71) Applicant: Conopco, Inc., Englewood Cliffs, NJ (US)

(72) Inventors: Praful Gulab Rao Lahorkar, Bangalore (IN); Ashish Anant Vaidya, Bangalore (IN); Mohan Vijaykumar Chavan, Mumbai (IN); Vijay Ramchandra Gadgil, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/891,976

(22) PCT Filed: Apr. 24, 2014

(86) PCT No.: PCT/EP2014/058319
§ 371 (c)(1),
(2) Date: Nov. 18, 2015

(87) PCT Pub. No.: WO2014/191143
PCT Pub. Date: Dec. 4, 2014

(65) Prior Publication Data
US 2016/0081896 A1    Mar. 24, 2016

(30) Foreign Application Priority Data
May 27, 2013 (EP) .................................. 13169320

(51) Int. Cl.
| | | |
|---|---|---|
| *A61K 9/50* | (2006.01) | |
| *A61K 8/35* | (2006.01) | |
| *A61K 8/60* | (2006.01) | |
| *A61Q 17/04* | (2006.01) | |
| *A61K 8/365* | (2006.01) | |
| *A61K 8/97* | (2006.01) | |

(52) U.S. Cl.
CPC .............. *A61K 8/35* (2013.01); *A61K 8/365* (2013.01); *A61K 8/602* (2013.01); *A61K 8/97* (2013.01); *A61Q 17/04* (2013.01); *A61K 2800/52* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 4,867,964 A | 9/1989 | Forestier | |
| 5,952,391 A | 9/1999 | Gers-Barlag | |
| 2009/0039322 A1 | 2/2009 | Bonda | |
| 2009/0209651 A1 | 8/2009 | Siegner | |
| 2010/0330018 A1 | 12/2010 | Lorant | |
| 2015/0037267 A1* | 2/2015 | Gadgil .................. | A61K 8/602 424/59 |

FOREIGN PATENT DOCUMENTS

| | | | |
|---|---|---|---|
| EP | 0502205 | 9/1992 | |
| EP | 0514491 | 11/1992 | |
| EP | 0980684 | 2/2000 | |
| FR | 2942961 | 9/2010 | |
| FR | 2942961 A1 * | 9/2010 | ............... A61K 8/35 |
| JP | 6321764 | 11/1994 | |
| JP | 06321764 A * | 11/1994 | |
| JP | 10101543 | 4/1998 | |
| JP | 2000095721 | 4/2000 | |
| JP | 2008247839 | 10/2008 | |
| WO | WO2008104941 | 9/2008 | |

OTHER PUBLICATIONS

Mishra et al., "A Plant Review: Butea Monosperma (Lam.)Kuntze", Research Journal of Pharmaceutical, Biological and Chemical Sciences, 2012, pp. 1-15; XP055091345. pp. 1 to 15.
Chokchaisiri et al., "Bioactive Flavonoids of the Flowers of Butea monosperma", Chem. Pharm. Bull. 2009 vol. 57 No. 4 pp. 428-432. pp. 16 to 20.
Khatib et al., "Chalcones as potent tyrosinase inhibitors : the importance of a 2,4-substituted resorcinol moiety", Bioorganic & Medicinal Chemistry, 2005, vol. 13 No. 2, pp. 433-441. pp. 1 to 9.
Search Report in EP13169320 dated Dec. 4, 2013. pp. 10 to 12.
Search Report in PCTEP2014058319 dated Jun. 3, 2014. pp. 13 to 16.
Sindhia et al., "Plant Review Butea monosperma", International Journal of Pharmaceutical and Clinical Research 2010, vol. 2 Iss 2 pp. 90-94. pp. 17 to 21.
Written Opinion in EP13169320 dated Dec. 4, 2013. pp. 22 to 22.
Written Opinion in PCTEP2014058319 dated Jun. 3, 2014. pp. 23 to 29.
IPRP1 in PCTEP2014058319 dated Dec. 1, 2015.

* cited by examiner

*Primary Examiner* — Robert A Wax
*Assistant Examiner* — Quanglong Truong
(74) *Attorney, Agent, or Firm* — Greenberg Traurig, LLP

(57) ABSTRACT

The invention relates to a photoprotective personal care composition that provides enhanced stability of the UV-A sunscreen present therein. The present inventors have found that it is possible to enhance stability of the UV-A sunscreen of the dibenzoylmethane group by including certain compounds of the chalcone group.

10 Claims, No Drawings

PHOTOPROTECTIVE PERSONAL CARE COMPOSITION

FIELD OF THE INVENTION

The invention relates to a photoprotective personal care composition that provides enhanced stability of the UV-A sunscreen present therein.

BACKGROUND OF THE INVENTION

Solar radiation includes ultraviolet (UV) radiation, wavelength of which is between 200 nm and 400 nm. Exposure of skin to UV-A (320 to 400 nm) and UV-B (290 to 320 nm) causes various problems like reddening of the skin, localized irritation, sunburn, melanoma and formation of wrinkles. UV radiation is also known to cause damage to hair. Therefore, it is desirable to protect the skin and other keratinous substrates of the human body from the harmful effects of both UV-A and UV-B radiation.

Cosmetic compositions comprising sunscreen agents are used to protect the skin against UV radiation. The most commonly used UV-A sunscreen is of the dibenzoylmethane class. They are often used along with UV-B sunscreens to get wide spectrum sunscreen protection. It has been reported that stability of dibenzoylmethane compounds in sunscreen compositions is low when applied to the skin and exposed to solar radiation. The stability is poorer when an oil-soluble UV-B organic sunscreen especially from the class of cinnamic acid, is included.

Synthetic sunscreen stabilizers have been reported to solve this problem, e.g. as disclosed in EP 0514491 (L'Oreal, 1991) and more recently in US2009/039322 (Hallstar).

While the above references are directed to improving stability of sunscreen containing compositions, it is desirable to use stabilizers that are available in nature or extractable from natural sources like plants that the consumers consider to be milder and therefore is expected to have less irritation and allergenic potential when applied on the skin. Stabilisers which are available in nature or extractable from natural sources is also expected to be widely available and therefore can be provided to the consumers at low cost. Topical compositions comprising extracts from plant material are known for various purposes.

The present inventors have found that it is possible to enhance stability of the UV-A sunscreen of the dibenzoylmethane group by including certain compounds of the chalcone group.

U.S. Pat. No. 5,952,391 (Beiersdorf, 1999) discloses use of flavone derivatives and flavanone derivatives, in particular flavonoids for stabilizing cosmetic or dermatologically acceptable substances, the chemical formula of which includes the structural moiety of dibenzoylmethane, against the decomposition caused by UV radiation.

U.S. Pat. No. 4,867,964 (L'Oreal, 1989) discloses a cosmetic composition containing 2-hydroxylated chalcone derivatives and its use for protecting the skin and the hair against luminous radiations, new 2-hydroxylated chalcone derivatives and a process for their preparation.

These publications have not disclosed use of actives claimed in the present invention or natural extracts comprising the actives for stabilizing UV-A sunscreens.

It is thus an object of the present invention to obviate the drawbacks of the prior art and provide a highly photostable sunscreen composition while ensuring prolonged efficacy of the UV-A organic sunscreen used therein.

Another object of the present invention is to achieve the above object while additionally keeping costs low.

SUMMARY OF THE INVENTION

The present invention relates to a photostable sunscreen composition comprising
(i) 0.1 to 10% by weight of dibenzoylmethane or its derivative;
(ii) 0.1 to 10% by weight of a chalcone compound of the formula:

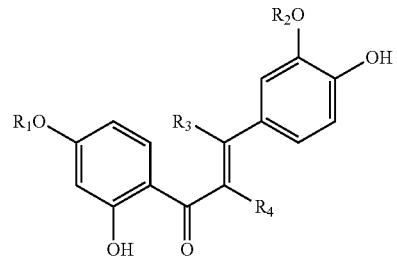

where R1 is selected from
a H atom,
a glucose unit,

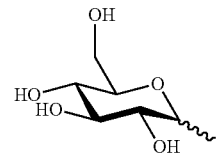

or an isoprene unit;
R2 is selected from a H atom or a glucose unit;
R3 and R4 are each independently selected from a H atom or an aryl group; and
(iii) a cosmetically acceptable base.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

By "A Sunscreen Composition" as used herein, is meant to include a composition for topical application to sun-exposed areas of the skin and/or hair of mammals, especially humans. Such a composition may be generally classified as leave-on or rinse off, and includes any product applied to a human body for also improving appearance, cleansing, odor control or general aesthetics. It is more preferably a leave-on product. The composition of the present invention can be in the form of a liquid, lotion, cream, foam, scrub, gel, or toner, or applied with an implement or via a face mask, pad or patch. Non-limiting examples of such sunscreen compositions include leave-on skin lotions, creams, antiperspirants, deodorants, lipsticks, foundations, mascara, sunless tanners and sunscreen lotions. "Skin" as used herein is meant to include skin on the face and body (e.g., neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of providing photoprotection.

An advantage of the present invention is that inclusion of the chalcone compound according to the invention ensures that the UV-A sunscreen does not get much degraded in the presence of UV radiation thereby providing UV-protection for long period of time to the substrate of interest.

The photostable sunscreen composition of the invention comprises UV-A sunscreen dibenzoylmethane or its derivative; the chalcone compound sunscreen stabliser and a cosmetically acceptable base.

The sunscreen composition of the invention comprises a UV-A sunscreen which is a dibenzoylmethane or its derivatives. Preferred dibenzoylmethane derivatives are selected from 4-tert-butyl-4'-methoxydibenzoylmethane, 2-methyl-dibenzoylmethane, 4-methyl-dibenzoyl-methane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxydibenzoylmethane. The most preferred dibenzoylmethane derivative is 4-tert.-butyl-4'-methoxydibenzoylmethane. The composition of the invention comprises 0.1 to 10%, more preferably 0.2 to 5%, further more preferably, 0.4 to 3%, by weight dibenzoylmethane or a derivative thereof based on total weight of the composition and including all ranges subsumed therein.

The chalcone compound is present in 0.1 to 10%, more preferably 0.1 to 5%, further more preferably 0.2 to 3% by weight of the sunscreen composition.

The chalcone compound sunscreen stabiliser has the formula

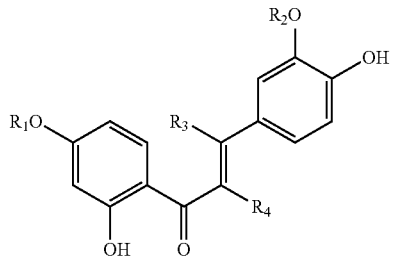

where R1 is selected from
(a) a H atom,
(b) a glucose unit,

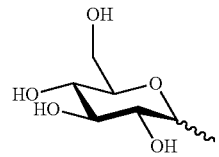

or
(c) an isoprene unit;
R2 is selected from a H atom or a glucose unit;
R3 and R4 are each independently selected from a H atom or an aryl group.

When the R1 in the chalcone compound is an isoprene unit, it is selected from

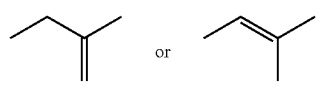

It is preferred that R3 and R4 are each a H atom.

The most preferred chalcone compounds for use as a sunscreen stabiliser in the composition of the present invention are:
(a) butein where R1, R2, R3 and R4 are each a hydrogen atom; or
(b) monospermoside where R1 is a glucose unit and R2, R3 and R4 are each a hydrogen atom.

Thus the structures of butein and monospermoside are as follows:

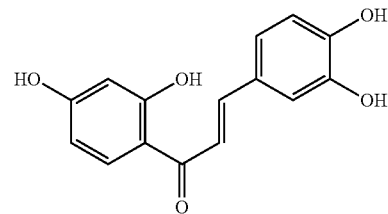

Butein m/z = 272

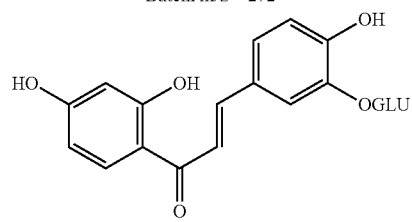

Monospermoside (m/z = 434)

The butein and monospermoside may be isolated from aqueous extract of the flower of *Butea monosperma*. Aqueous extract from flowers of *Butea monosperma* contain many compounds like dihydromonospermoside, butein, monospermoside, isoliquiritigenin, 7,3',4'-trihydroxyflavone, four flavanones, butin, butrin, isomonospermoside, liquiritigenin, formononetin, afrormosin and formononetin-7-O-beta-D-glucopyranoside. Of the various compounds listed above, the present inventors have determined that only the chalcones fitting the structure claimed in the present invention act as good sunscreen stabilisers, of which butein and monospermoside are the best ones.

*Butea monosperma* is a species of *Butea* native to tropical and sub-tropical parts of the Indian Subcontinent and Southeast Asia. Common names include Palash, Dhak, Palah, Flame of the Forest, and Bastard Teak.

It is a medium sized dry season-deciduous tree, growing to about 15 m high. It is a slow growing tree. It is used for timber, resin, fodder, medicine, and dye. The gum from the tree is used in certain food dishes. The gum is also known as Bengal Kino and is considered valuable by druggists because of its astringent qualities and by leather workers because of its tannin.

The sunscreen composition preferably additionally comprises a UV-B organic sunscreen selected from the class of cinnamic acid, salicylic acid, diphenyl acrylic acid or derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX. The UV-B organic sunscreen is preferably included in 0.1 to 10%, more preferably 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the chalcone compound sunscreen stabiliser is found to be very efficacious in stabilizing the sunscreen composition even when UV-B sunscreens are present.

The composition of the invention comprises a cosmetically acceptable base. The cosmetically acceptable bases are such as to have a product in preferably a cream, lotion, gel or emulsion format, more preferably an emulsion format. The cosmetically acceptable base may be an oil-in-water emulsion or a water-in-oil emulsion. The chalcone compound sunscreen stabilisers are found to be more efficacious in stabilising sunscreen when present in water-in-oil emulsions.

An especially useful water-in-oil emulsion is one which comprises silicone oils. A highly suitable silicone based emulsion is one which contains 5-50% silicone elastomer blend swollen in suitable volatile silicone or volatile organic alternates. Silicone elastomers differ from linear polymers because of cross-linking. Many silicone elastomers are made from linear silicone polymers that contain reactive sites along the polymer chain. Elastomers have very different physical and chemical properties from linear polymers, and the properties of elastomers depend very much on the number of cross-links. An elastomer with a relatively small number of cross-links will be very soft and will swell significantly in the presence of a compatible solvent. As the number of cross-links increases, the hardness of the elastomer increases, and the elastomer will swell to a lesser extent in the presence of volatile silicone or volatile organic alternates.

A suitable silicone elastomers for use in the composition of the invention is DC 9045, a dimethicone crosspolymer commercially available from Dow Corning. DC 9045 is chemically a blend of cyclopentasiloxane swelling agent and dimethicone crosspolymer. The swelling agent is most preferably a silicone fluid or a functional silicone fluid. Swelling agent is most preferably low molecular weight silicone oil which includes (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS). By "low molecular weight" in the this paragraph is meant a compound having a molecular weight from 1000 to 9000. The preferred swelling agents are volatile silicones are (a) decamethyl cyclopentasiloxane (commercially known as $D_5$ available from Dow Corning DC245); (b) dodecamethyl cyclohexasiloxane (commercially known as $D_6$ and available from Dow corning); (c) TMF-1.5 (INCI: Methyl Trimethicone); (d) DM-Fluids-$A_6$ (INCI: Dimethicone); (e) DM-Fluid-2cs (INCI: Dimethicone); (f) SF1000N1 (INCI: Trisiloxane (1 cSt); (g) SF1000N1.5 (INCI: Dimethicone (1.5 cSt); (h) SF1000N2 (INCI: Dimethicone (2 cSt); and DM-Fluid-5 cSt (INCI: Dimethicone). Most preferred volatile silicones are (a) decamethyl cyclopentasiloxane (commercially known as D5 available from Dow Corning DC245; (b) DM-Fluid-2cs; and (c) DM-Fluid ~5 cst (INCI: Dimethicone). The volatile silicone is preferably present in 10 to 23%, more preferably in 19 to 22% by weight of the composition.

Other swelling agents such as, volatile organic alternates to volatile silicones which are ester emmolints; include PPG-3 Benzyl Ether Ethylhexanoate (Crodamol SFX); PPG-3 Benzyl Myristate[9-11] (Crodamol STS); Propanediol Dicaprylate/Diisostearyl Malate (Pelemol D5RV); Caprylic/Capric Triglycerides (Crodamol GTCC or CCT); Ethyl Hexyl Hydroxy Stearate (EHHS) show solubility parameters of ~18.1-18.8 M $Pa^{1/2}$. Most of these ester emollients also have potential as the alternative to decamethylcyclopentasiloxane ($D_5$) due to their exceptional spreading properties, sensory, and solubility/miscibility in a wide range of cosmetic raw materials. These solvents were therefore selected to develop miscible cosolubilized oil phase for water-in-oil formulations.

Other useful silicone elastomer blends which may be used in the present invention are commercially available as DC 9027 (a blend of an ultra high viscosity dimethiconol and silicone elastomer in cyclopentasiloxane) available from Dow Corning DC 9546 (a blend of high molecular weight silicone elastomer, cyclopentasiloxane and a high molecular weight linear silicone polymer) available from Dow Corning, EL8050 (a blend of high molecular weight polyglycol-modified silicone elastomer in isododecane) available from Dow Corning and EL8051 (a blend of high molecular weight polyglycol-modified silicone elastomer in isodecyl neopentanoate) available from Dow Corning.

The composition preferably comprises 10 to 70%, more preferably 30 to 50% water by weight of the composition.

The water-in-oil emulsion is preferably emulsified with a non-ionic surfactant having an HLB value of at most 6. Suitable non-ionic surfactants falling within this criteria are:

The water-in-oil emulsion is preferably emulsified with a non-ionic surfactant having an HLB value of at most 6. Suitable non-ionic surfactants falling within this criteria are:

Dimethicone copolyol; PEG-11 methyl ether dimethicone PEG/PPG-20/22 Butyl ether dimethicone; PEG-9 dimethicone; PEG-3 dimethicone; PEG-9 methyl ether dimethicone; PEG-10 dimethicone, PEG-10 dimethicone; PEG-32 methyl ether dimethicone; Sorbitan Monooleate; •Glyceryl Monooleate; •Lanolin & Lanolin Alcohols Glycol Distearate HLB=1 Sorbitan Trioleate HLB=1.8 Propylene Glycol Isostearate HLB=2.5 Glycol Stearate HLB=2.9 Sorbitan Sesquioleate HLB=3.7 Glyceryl Stearate HLB=3.8 Lecithin HLB=4 Lecithin (HLB approx. 4.0) Sorbitan Oleate HLB=4.3 Sorbitan Stearate (HLB 4.7); Sorbitan Monostearate NF HLB=4.7 Sorbitan Stearate HLB=4.7 Sorbitan Isostearate HLB=4.7 Steareth-2 HLB=4.9 Oleth-2 HLB=4.9 Glyceryl Laurate HLB=5.2 Polyglyceryl Oleate (HLB 5.0); Ceteth-2 HLB=5.3 PEG-30 Dipolyhydroxystearate HLB=5.5 Glyceryl Stearate SE HLB=5.8 Sorbitan Stearate (and) Sucrose Cocoate HLB=6 PEG-4 Dilaurate HLB=6

The cosmetically acceptable base is usually from 10 to 99%, preferably from 50 to 99% by weight of the composition. The cosmetically acceptable base preferably includes water. Water is preferably included in 35 to 90%, more preferably 50 to 85%, further more preferably 50 to 80% by weight of the composition.

Other useful sun-protective agents e.g. inorganic or organic particulate sun-blocks may be preferably used in the composition of the present invention. These include, for example, polystyrene particles which as coated or uncoated with inorganic materials, zinc oxide, iron oxide, silica, such as fumed silica, or titanium dioxide. The total amount of sun block that is preferably incorporated in the composition according to the invention is from 0.1 to 5% by weight of the composition.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The composition of the invention may comprise a conventional deodourant base as the cosmetically acceptable carrier. By a deodorant is meant a product in the stick, roll-on, or propellant medium which is used for personal deodorant benefit e.g. application in the under-arm or any other area which may or may not contain anti-perspirant actives. Deodorant compositions can generally be in the form of firm solids, soft solids, gels, creams, and liquids and are dispensed using applicators appropriate to the physical characteristics of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

According to a preferred aspect of the present invention there is provided a composition where the chalcone compounds are included as an extract of flowers of *Butea monosperma*. A preferred process to prepare the extract comprises the steps of
(a) extracting flowers of *Butea monosperma* with water at a temperature in the range of 20 to 40° C.;
(b) concentrating the aqueous extract to dryness to prepare a dry powder;
(c) dissolving the dry powder in a hydroalcoholic solution;
(d) extracting the desired extract with diethyl ether.

According to yet another aspect of the present invention there is provided a A method of stabilizing a dibenzoylmethane or its derivative by including a chalcone compound of the formula:

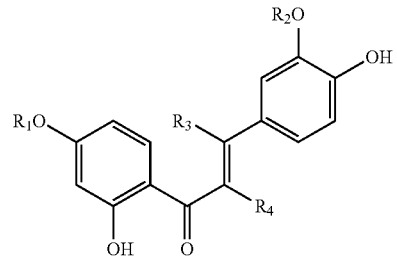

where R1 is selected from
a H atom,
a glucose unit,

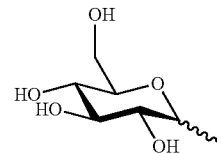

or an isoprene unit;
R2 is selected from a H atom or a glucose unit;
R3 and R4 are each independently selected from a H atom or an aryl group;
in a sunscreen composition comprising the dibenzoylmethane or its derivative.

The invention is now further described by way of the following non-limiting examples.

EXAMPLES

Example 1 to 5

Photostability of UVA-Sunscreen Parsol 1789 in Presence of Various Fractions of *Butea monosperma*

Fraction 1:
100 of dry *Butea monosperma* flowers were extracted with 800 mL water at room temperature under the vacuum (800 mbarr) for 24 hours. ~730 mL of aqueous extract was separated from the flowers. The aqueous extract was evaporated to dryness to obtain ~25 g of solids. This solid was dissolved in 200 mL water and passed through column packed with MCI gel. The MCI bed was rinsed with water to remove un-adsorbed sugar. The adsorbed fraction was eluted with ethanol to obtain a fraction which was evaporated to dryness to obtain ~23 g of solids.

This solid was dissolved in 10% ethanolic aqueous solution (500 mL) followed by solvent extraction with diethyl ether to obtain the desired Fraction-1. Fraction 1 was analysed to contain 25 weight % Butein. The Fraction-1 was evaporated to dryness to obtain ~8 g of solid powder.

Fraction 2:

The remaining aqueous extract (500 mL) was further solvent extracted with ethyl acetate and then with butanol to obtain a Fraction-2 which was analysed to contain 15 weight % monospermoside.

The ability of the fractions of *Butea monosperma* to stabilize Parsol 1789 (4-tert.-butyl-4'-methoxydibenzoylmethane) was measured in comparison to a well known commercial stabilizer (Octocrylene) using the method below:

The method was based on spotting the HPTLC plates (in duplicate) with the sunscreen molecules of interest along with potential quencher molecules or formulations. The plate is then exposed to UVR (intensity 5.5 mW/cm$^2$) for 120 minutes. Following this the chromatographic separation was carried out using appropriate solvent system.

Densitometry analysis is done to determine the amount of sunscreen degraded. Stock solutions were prepared in methanol following the ratios as mentioned in the following table. 14 μL of stock solutions were loaded (3 mm width; 16 mm separation) on a 10×10 cm F254 HPTLC plate, using CAMAG LINOMAT 5 applicator equipped with a 100 μL micro-syringe (Hamilton, Switzerland). Ascending chromatography was performed at a distance of 85 mm in a TLC chamber using n-hexane-ethyl acetate 9:1 (v/v) as the mobile phase (~10 mL). The plates were dried at room temperature and subjected to ultraviolet absorption densitometry scan. The concentration dependent fluorescent bands due to presence of sunscreens were detected with a linear scan at 310 or 357 nm, using Camag TLC Scanner 3, in the presence of deuterium source. Slit width of 8×0.4 mm and scanning rate of 20 mm s$^{-1}$ were maintained during each densitometry scan. Parsol 1789 concentrations present on each lane were determined from densitogram peak areas; prior and after the sun exposure using Win CATS Planar chromatography manager software.

The data on the stability of the various compositions are presented in the following table-1:

TABLE 1

| Example No. | Samples | Mean % stability |
|---|---|---|
| 1 | Parsol 1789 (400 ppm) | 56 |
| 2 | Parsol 1789 (400 ppm) + Parsol MCX (400 ppm) | 23 |
| 3 | Parsol 1789 (400 ppm) + Octocrylene (400 ppm) | 75 |
| 4 | Parsol 1789 (400 ppm) + Fraction - 1 (1200 ppm) containing 25% Butein | 81 |
| 5 | Parsol 1789 (400 ppm) + Fraction - 2 (1200 ppm) containing 15% Monospermoside | 90 |

Parsol MCX is 2-ethyl-hexyl-4-methoxy cinnamate.

Octocrylene is 2-Ethylhexyl-2-cyano-3,3-diphenylacrylate

The data in Table-1 indicates that Parsol 1789 is highly unstable (Example-1) especially in the presence of Parsol MCX (Example-2). Commercially available stabilizer Octocrylene (Example-3) enhances the stability but the stabilisers as per the present invention are vastly superior (Examples 4 and 5).

Example 6-11

Parsol 1789 Stabilized with Pure Compounds (Various Flavanoids Including Those Present in *Butea monosperma*)

Various pure compounds like butrin, isomonospermoside, isobutein, butein and monospermoside present in extract of *Butea monosperma* were tested for stability of Parsol 1789. Further one other commonly known flavanoid quercetin was also tested. The stability was measured similar to the method used for examples 1 to 5. The data is summarized in Table-2 along with data for Examples 1 to 3.

The structures of the various compounds is given below:

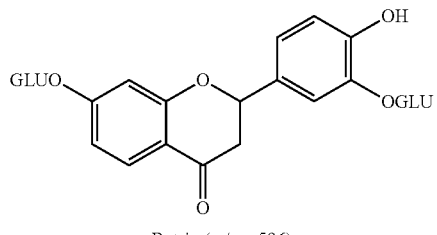

Butrin (m/z = 596)

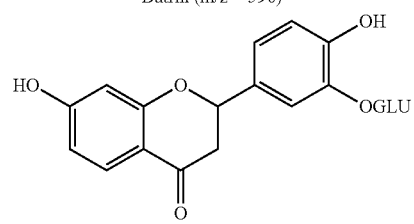

Isomonospermoside (m/z - 434)

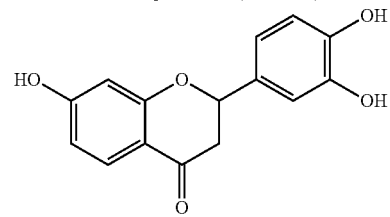

Isobutein (m/z = 272)

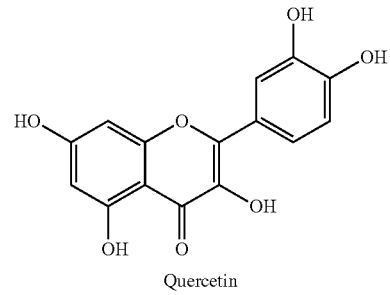

Quercetin

TABLE 2

| Example No. | Samples | Mean % stability |
|---|---|---|
| 1 | Parsol 1789 (400 ppm) | 56 |
| 2 | Parsol 1789 (400 ppm) + Parsol MCX (400 ppm) | 23 |
| 3 | Parsol 1789 (400 ppm) + Octocrylene (400 ppm) | 75 |

TABLE 2-continued

| Example No. | Samples | Mean % stability |
|---|---|---|
| 6 | Parsol 1789 (400 ppm) + Butrin (1200 ppm) | 67 |
| 7 | Parsol 1789 (400 ppm) + Isomonospermodide (1200 ppm) | 68 |
| 8 | Parsol 1789 (400 ppm) + Isobutein - (1:4) (1200 ppm) | 31 |
| 9 | Parsol 1789 (400 ppm) + Quercetin (400 ppm) | 69 |
| 10 | Parsol 1789 (400 ppm) + Monospermoside (1200 ppm) | 83 |
| 11 | Parsol 1789 (400 ppm) + Butein (1200 ppm) | 91 |

The data in Table-2 above indicates that compounds as per the present invention (Example 10 and 11) are vastly superior to other flavanoids which are commonly known.

Examples 12 and 13

Use of the Stabilizers of the Invention in Oil-in-Water Emulsion Sunscreen Composition as Compared to Water-in-Oil Emulsion A oil-in-water emulsion sunscreen composition as shown in Table-3 below was prepared.

TABLE 3

|  | Example 12, wt % |
|---|---|
| Hystric acid | 17.0 |
| Isopropyl myristate | 1.6 |
| Parsol 1789 | 1.2 |
| Parsol MCX | 2.2 |
| Fraction-1 (~25 wt % Butein) | 1.5 |
| Phenoxy ethanol | 4.4 |
| Glycerine | 1.0 |
| KOH (85%) | 0.6 |
| Dimethicone | 0.5 |
| Water | To 100 |

Hystric acid is a fatty acid mixture containing 45% stearic acid and 55% palmitic acid.

This composition was stored at room temperature (~25° C.) for 30 days. % Butein present in the extract was quantified before and after the storage. It was observed that there was about 70% loss of butein in the composition due to chemical transformation on storage.

An water-in-oil sunscreen composition as shown in Table 4 below was prepared:

TABLE 4

|  | Example 13, wt % |
|---|---|
| EL 8051 | 40.0 |
| 5225C | 10.0 |
| Parsol 1789 | 1.2 |
| Parsol MCX | 2.2 |
| Fraction-1 (~25 wt % Butein) | 1.5 |
| Propylene Carbonate | 6 |
| Water | To 100 |

* Polymer EL8051: is Isodecyl neopentanoate and dimethicone/bis isobutyl PPG-20 cross polymer available from Dow Corning.
** Silicone 5225C is a Cyclopentasiloxane and PEG/PPG-18/18 dimethicone polymer.

This above composition was stored at room temperature (~25° C.) for 30 days. % Butein present in the extract was quantified before and after the storage. It was observed that there was about 90% stability of butein in the formulation after 30 days of storage.

Quantification of Photostability of Compositions

The compositions as per Example 12 and 13 above were applied (~2 mg/cm$^2$) on four clean glass plates to generate thin films of uniform thickness. Out of these, three plates were exposed to Atlas solar simulated radiations (UVA flux, 5.5 mW/cm$^2$). One plate was removed after 30, 60 and 120 minutes of UV exposure, each. Fourth plate was kept un-exposed which served as the control sample. Subsequent to completion of the above protocol, all four films of the cream were separately dissolved in suitable HPLC grade methanol. The UVA sunscreen (4-t-butyl, 4'-methoxydibenzoylmethane) quantification was done using Perkin Elmer UV/Visible Spectrometer. The absorbance at a scanning range of 200-800 nm was measured for each solution, using quartz cuvette, and respective blank solutions spectrometer. From the spectrum the % of UV-A compound i.e. Parsol-1789 remaining was read at various times (for a representative wavelength i.e. 355 nm) and summarized in Table-5 below.

TABLE 5

| % UVA remaining after | Example-12 | Example 13 |
|---|---|---|
| 30 minutes | 47 | 87 |
| 60 minutes | 26 | 66 |
| 120 minutes | 11 | 43 |

The data presented in the Table above along indicates that the ability of butein to stabilize Parsol 1789 is superior in water-in-oil emulsions (Example 13) as compared to oil-in-water emulsions (Example 12).

Examples 14-16

Stability of Parsol-1789 in Various UV-A and UV-B Containing Water-in-Oil Emulsion Sunscreen Compositions Photoprotective personal care compositions in water-in-oil emulsion compositions were prepared as shown in Table-6.

TABLE 6

|  | Example 14, wt % | Example 15, wt % | Example 16, wt % |
|---|---|---|---|
| EL 8051 | 40 | 40 | 40 |
| 5225C | 10 | 10 | 10 |
| Parsol 1789 | 1.2 | 1.2 | 1.2 |
| Parsol MCX | 2.2 | 2.2 | 2.2 |
| Fraction-1 (~25 wt % Butein) | — | 1.5 | — |
| Octocrylene | — | — | 1.5 |
| Propylene Carbonate | 6 | 6 | 6 |
| Water | To 100 | To 100 | To 100 |

The photostability of the various compositions of Table-6 was measured using the same procedure as used for Example 13 and are summarized in Table-7 below:

TABLE 7

| % UVA remaining after | Example 14 | Example 15 | Example 16 |
| --- | --- | --- | --- |
| 30 minutes | 62 | 81 | 55 |
| 60 minutes | 30 | 69 | 29 |
| 120 minutes | 21 | 39 | 12 |

The data in above Table-7 indicates that composition as per the invention (Example-15 provides for improved photostability as compared to a composition without butein (Example 14) or a composition with a well known UV-A stabilizer, Octocrylene (Example-16).

Example 17

Hair Care Composition

A hair care composition, as per the invention, as shown in Table-8, was made in the form of a hair styling gel. Aristoflex AVC (cationic copolymer) was dissolved in water using a homogenizer. Parsol 1789 and butea extract were separately dissolved in propylene carbonate. The above two mixtures were then mixed and homogenized by using a high speed homogenizer.

TABLE 8

| Ingredients | Percentage |
| --- | --- |
| Water | To 100 |
| Aristoflex AVC (cationic polymer) | 1.2 |
| Propylene carbonate (oil phase) | 9 |
| Parsol 1789 ™ | 1.2 |
| Fraction-1 (~25 wt % Butein) | 1.2 |

The invention claimed is:

1. A photostable sunscreen composition comprising
(i) 0.1 to 10% by weight of dibenzoylmethane or its derivative;
(ii) 0.1 to 10% by weight of a chalcone compound of the formula:

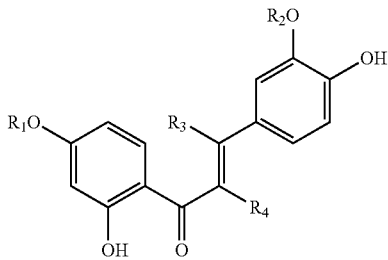

where R1 is selected from
a glucose unit,

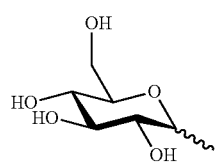

or an isoprene unit;
R2 is selected from a H atom or a glucose unit;
R3 and R4 are each independently selected from a H atom or an aryl group; and
(iii) a cosmetically acceptable base.

2. The composition as claimed in claim 1 wherein said chalcone compound is monospermoside where R1 is a glucose unit and R2, R3 and R4 are each a H atom.

3. The composition as claimed in claim 1 additionally comprising a UV-B organic sunscreen selected from cinnamic acid, salicylic acid, diphenyl acrylic acid or derivatives thereof.

4. The composition as claimed in claim 3 wherein said UV-B sunscreen is 2-ethyl-hexyl-4-methoxy cinnamate.

5. The composition as claimed in claim 3 wherein said UVB organic sunscreen is present in 0.1 to 10% by weight of the composition.

6. The composition as claimed in claim 1 wherein said cosmetically acceptable base is a water-in-oil emulsion.

7. The composition as claimed in claim 6 comprising a non-ionic surfactant having an HLB value of at most 6.

8. The composition as claimed in claim 1 wherein said chalcone is present as an extract of the plant *Butea monosperma*.

9. The composition as claimed in claim 8 wherein said extract is prepared by a process comprising the steps of
(a) extracting flowers of *Butea monosperma* with water at a temperature in the range of 20 to 40° C.;
(b) concentrating the aqueous extract to dryness to prepare a dry powder;
(c) dissolving the dry powder in a hydroalcoholic solution;
(d) extracting the desired extract with diethyl ether.

10. A method of stabilizing a dibenzoylmethane or its derivative by including a chalcone compound of the formula:

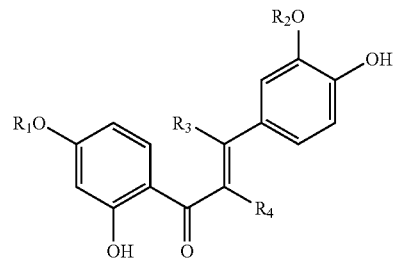

where R1 is selected from
a glucose unit,

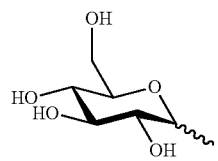

or an isoprene unit;
R2 is selected from a H atom or a glucose unit;
R3 and R4 are each independently selected from a H atom or an aryl group;
in a sunscreen composition comprising the dibenzoylmethane or its derivative.

* * * * *